(12) United States Patent
Passmore et al.

(10) Patent No.: US 7,522,040 B2
(45) Date of Patent: Apr. 21, 2009

(54) REMOTELY COMMUNICATING, BATTERY-POWERED NANOSTRUCTURE SENSOR DEVICES

(75) Inventors: John Loren Passmore, Berkeley, CA (US); Jean-Christophe P. Gabriel, Pinole, CA (US); Alexander Star, Albany, CA (US); Vikram Joshi, San Francisco, CA (US); Sergei Skarupo, San Francisco, CA (US)

(73) Assignee: Nanomix, Inc., Emeryville, CA (US)

( * ) Notice: Subject to any disclaimer, the term of this patent is extended or adjusted under 35 U.S.C. 154(b) by 597 days.

(21) Appl. No.: 11/111,121

(22) Filed: Apr. 20, 2005

(65) Prior Publication Data

US 2006/0055392 A1 Mar. 16, 2006

Related U.S. Application Data

(60) Provisional application No. 60/652,883, filed on Feb. 15, 2005, provisional application No. 60/564,248, filed on Apr. 20, 2004.

(51) Int. Cl.
*G08B 21/00* (2006.01)

(52) U.S. Cl. ............... 340/540; 340/603; 340/628; 340/632; 340/539.26; 324/71.1

(58) Field of Classification Search ............ 340/603, 340/540, 506, 539.12, 539.11, 539.26, 573.1, 340/628, 629, 630, 631, 632, 541; 324/71.1; 422/98, 82.02, 82.03; 257/253, 347, 401, 257/414; 73/105

See application file for complete search history.

(56) References Cited

U.S. PATENT DOCUMENTS

| | | | |
|---|---|---|---|
| 3,860,430 A | 1/1975 | Walker et al. | |
| 4,795,968 A | 1/1989 | Madou et al. | |
| 4,851,195 A | 7/1989 | Matthews et al. | |
| 4,935,345 A | 6/1990 | Guilbeau et al. | |
| 5,246,859 A | 9/1993 | Nelson et al. | |
| 5,382,417 A | 1/1995 | Haase | |
| 5,425,869 A | 6/1995 | Noding et al. | |

(Continued)

FOREIGN PATENT DOCUMENTS

EP 1558933 8/2005

(Continued)

OTHER PUBLICATIONS

"Gas and Humidity Sensors Based on Iron Oxide-Polyprrole Nanocomposites" By Suri, K. et al., Sensors and Actuators B 81 (2002) 277-282.

(Continued)

*Primary Examiner*—Anh V La
(74) *Attorney, Agent, or Firm*—Weaver Austin Villeneuve & Sampson LLP

(57) ABSTRACT

A portable sensor device incorporates a low-power, nanostructure sensor coupled to a wireless transmitter. The sensor uses a nanostructure conducting channel, such as a nanotube network, that is functionalized to respond to a selected analyte. A measurement circuit connected to the sensor determines a change in the electrical characteristic of the sensor, from which information concerning the present or absence of the analyte may be determined. The portable sensor device may include a portable power source, such as a battery. It may further include a transmitter for wirelessly transmitting data to a base station.

28 Claims, 5 Drawing Sheets

U.S. PATENT DOCUMENTS

| | | | |
|---|---|---|---|
| 5,618,496 A | 4/1997 | Hasumi et al. | |
| 5,674,752 A | 10/1997 | Buckley et al. | |
| 5,827,997 A | 10/1998 | Chung et al. | |
| 5,958,340 A | 9/1999 | Meyer et al. | |
| 5,993,694 A | 11/1999 | Ito et al. | |
| 6,010,459 A | 1/2000 | Silkoff et al. | |
| 6,031,454 A * | 2/2000 | Lovejoy et al. | 340/539.29 |
| 6,090,545 A | 7/2000 | Wohlstadter et al. | |
| 6,111,280 A * | 8/2000 | Gardner et al. | 257/253 |
| 6,136,962 A | 10/2000 | Shi et al. | |
| 6,217,828 B1 | 4/2001 | Bretscher et al. | |
| 6,286,226 B1 | 9/2001 | Jin | |
| 6,320,295 B1 | 11/2001 | McGill et al. | |
| 6,346,189 B1 | 2/2002 | Dai et al. | |
| 6,465,132 B1 | 10/2002 | Jin | |
| 6,489,394 B1 | 12/2002 | Andros | |
| 6,528,020 B1 * | 3/2003 | Dai et al. | 422/98 |
| 6,577,242 B2 * | 6/2003 | Jen et al. | 340/693.5 |
| 6,656,712 B1 | 12/2003 | Balavoine et al. | |
| 6,797,325 B2 | 9/2004 | Wang et al. | |
| 6,894,359 B2 | 5/2005 | Bradley et al. | |
| 7,109,859 B2 * | 9/2006 | Peeters | 340/539.11 |
| 7,271,720 B2 * | 9/2007 | Tabe | 340/540 |
| 2002/0017300 A1 | 2/2002 | Hickle et al. | |
| 2002/0092779 A1 | 7/2002 | Essalik et al. | |
| 2002/0117659 A1 | 8/2002 | Lieber et al. | |
| 2002/0130333 A1 | 9/2002 | Watanabe et al. | |
| 2003/0041438 A1 | 3/2003 | Wei et al. | |
| 2003/0068432 A1 | 4/2003 | Dai et al. | |
| 2003/0073919 A1 | 4/2003 | Hampton et al. | |
| 2003/0134267 A1 | 7/2003 | Kang et al. | |
| 2003/0134433 A1 | 7/2003 | Gabriel et al. | |
| 2003/0139003 A1 | 7/2003 | Gole et al. | |
| 2003/0171257 A1 | 9/2003 | Stirbl et al. | |
| 2003/0175161 A1 | 9/2003 | Gabriel et al. | |
| 2003/0180640 A1 | 9/2003 | Darty | |
| 2004/0011291 A1 | 1/2004 | Delaunay et al. | |
| 2004/0018587 A1 | 1/2004 | Makowski et al. | |
| 2004/0023428 A1 | 2/2004 | Gole et al. | |
| 2004/0043527 A1 | 3/2004 | Bradley et al. | |
| 2004/0065970 A1 | 4/2004 | Blanchet-Fincher | |
| 2004/0091285 A1 | 4/2004 | Lewis | |
| 2004/0120183 A1 | 6/2004 | Appenzeller et al. | |
| 2004/0132070 A1 | 7/2004 | Star et al. | |
| 2004/0136866 A1 | 7/2004 | Pontis et al. | |
| 2004/0158410 A1 | 8/2004 | Ono et al. | |
| 2004/0188780 A1 | 9/2004 | Kurtz | |
| 2004/0200734 A1 | 10/2004 | Co et al. | |
| 2004/0211580 A1 | 10/2004 | Wang et al. | |
| 2004/0219090 A1 | 11/2004 | Dziedzic et al. | |
| 2005/0129573 A1 | 6/2005 | Gabriel et al. | |
| 2005/0157445 A1 | 7/2005 | Bradley et al. | |
| 2005/0184641 A1 | 8/2005 | Armitage et al. | |
| 2005/0245836 A1 | 11/2005 | Star et al. | |
| 2005/0279987 A1 | 12/2005 | Star et al. | |
| 2006/0021881 A1 | 2/2006 | Soundarrajan et al. | |
| 2006/0263255 A1 | 11/2006 | Han et al. | |
| 2007/0048180 A1 | 3/2007 | Gabriel et al. | |
| 2007/0048181 A1 | 3/2007 | Chang et al. | |
| 2007/0114573 A1 | 5/2007 | Tzong-Ru et al. | |
| 2007/0132043 A1 | 6/2007 | Bradley et al. | |
| 2007/0208243 A1 | 9/2007 | Gabriel et al. | |
| 2008/0021339 A1 | 1/2008 | Gabriel et al. | |
| 2008/0093226 A1 | 4/2008 | Briman et al. | |

FOREIGN PATENT DOCUMENTS

| | | |
|---|---|---|
| EP | 1664724 | 6/2006 |
| EP | 1680353 | 7/2006 |
| EP | 1941270 | 7/2008 |
| JP | 2005-507121 | 11/2003 |
| JP | 2007505323 | 3/2007 |
| WO | WO97/32571 | 9/1997 |
| WO | WO01/32951 | 5/2001 |
| WO | WO01/44796 | 6/2001 |
| WO | WO02/15240 | 2/2002 |
| WO | WO02/079514 | 10/2002 |
| WO | WO02/095099 | 11/2002 |
| WO | WO03/016901 | 2/2003 |
| WO | WO03/046536 | 6/2003 |
| WO | WO03/078652 | 9/2003 |
| WO | WO2004/044586 | 5/2004 |
| WO | WO2005/026694 | 3/2005 |
| WO | WO2005/062031 | 7/2005 |
| WO | WO2005/094221 | 10/2005 |
| WO | WO2007/114931 | 10/2007 |
| WO | WO2007/136523 | 11/2007 |
| WO | WO2008/039165 | 4/2008 |
| WO | WO2008/052104 | 5/2008 |

OTHER PUBLICATIONS

European Search Report dated Mar. 30, 2007 issued in EP04788761.
International Search Report dated Nov. 6, 2007 issued in WO2005094221.
Preliminary Examination Report dated Nov. 6, 2007 issued in WO2005094221.
Written Opinion dated Nov. 6, 2007 issued in WO2005094221.
International Search Report and Written Opinion dated Jun. 11, 2008 issued in WO2008039165.
Preliminary Examination Report and Written Opinion dated Sep. 22, 2005 issued in WO2005026694.
International Search Report dated Sep. 22, 2005 issued in WO2005026694.
Preliminary Examination Report dated Nov. 16, 2006 issued in WO2004044586.
International Search Report dated Mar. 30, 2004 issued in WO2004044586.
US Office Action dated Jul. 24, 2008 issued in U.S. Appl. No. 10/656,898.
US Office Action dated Mar. 17, 2006 issued in U.S. Appl. No. 10/656,898.
US Office Action Final dated Oct. 20, 2006 issued in U.S. Appl. No. 10/656,898.
US Office Action dated May 7, 2007 issued in U.S. Appl. No. 10/656,898.
US Office Action dated Jan. 17, 2008 issued in U.S. Appl. No. 10/656,898.
US Advisory Action dated Apr. 8, 2008 issued in U.S. Appl. No. 10/656,898.
US Office Action dated Jun. 1, 2006 issued in U.S. Appl. No. 10/704,066.
US Office Action Final dated Jan. 24, 2007 issued in U.S. Appl. No. 10/704,066.
US Office Action dated Aug. 24, 2007 issued in U.S. Appl. No. 10/704,066.
US Office Action—Examiner Summary dated Mar. 6, 2008 issued in U.S. Appl. No. 10/704,066.
US Office Action dated Jun. 1, 2005 issued in U.S. Appl. No. 10/940,324.
US Office Action dated Mar. 3, 2006 issued in U.S. Appl. No. 10/940,324.
US Office Action dated Sep. 7, 2006 issued in U.S. Appl. No. 10/940,324.
US Office Action Final dated Feb. 21, 2007 issued in U.S. Appl. No. 10/940,324.
US Office Action dated Aug. 27, 2007 issued in U.S. Appl. No. 10/940,324.
US Office Action Final dated May 27, 2008 issued in U.S. Appl. No. 10/940,324.
US Office Action dated Dec. 2, 2005 issued in U.S. Appl. No. 10/945,803.
US Office Action Final dated Apr. 6, 2007 issued in U.S. Appl. No. 10/945,803.

US Office Action Final dated Sep. 12, 2007 issued in U.S. Appl. No. 10/945,803.
US Office Action dated Jun. 12, 2008 issued in U.S. Appl. No. 10/945,803.
US Notice of Allowance dated Jul. 7, 2008 issued in U.S. Appl. No. 10/945,803.
US Office Action dated Jul. 14, 2008 issued in U.S. Appl. No. 11/019,792.
US Office Action dated Jan. 18, 2008 issued in U.S. Appl. No. 11/090,550.
US Office Action dated Nov. 27, 2007 issued in U.S. Appl. No. 11/139,184.
US Office Action dated Apr. 15, 2008 issued in U.S. Appl. No. 11/139,184.
US Office Action dated Feb. 25, 2008 issued in U.S. Appl. No. 11/274,747.
US Office Action dated Mar. 4, 2008 issued in U.S. Appl. No. 11/318,354.
US Office Action dated May 12, 2008 issued in U.S. Appl. No. 11/437,275.
US Office Action dated Apr. 16, 2008 issued in U.S. Appl. No. 11/488,456.
Collins (2001), "Current Saturation and Electrical breakdown in Multiwalled Carbon Nanotubes," *Phys. Rev. Lett.*, v.86, 3127-3131, Apr. 2, 2001.
Collins (2001), "Engineering Carbon Nanotubes and Nanotube Circuits Using Electrical Breakdown," *Science*, 292, 706-709, Apr. 27, 2001.
Cui et al., "Nanowire Nanosensors for highly sensitive and selective detection of biological and chemical species," *Science 293*, (2001) p. 1289-1292, May 7, 2001.
Dai, H. (2002) "Carbon nanotubes: opportunities and challenges," *Surface Science*, v500, pp. 218-241, 2002.
Derycke et al. (2001) "Carbon Nanotube Inter- and Intramolecular Logic Gates," *Amer. Chem Soc Lets*, v1, No. 9 (Sep. 2001) pp. 453-456, 2001.
Kong (2001), "Functionalized Carbon Nanotubes for Molecular Hydrogen sensors," *Adv. Mater*, v13, 2001, pp. 1384-1386, Sep. 14, 2001.
Lin et al. (2002) "Functionalization Multiple-Walled Carbon Nanotubes with Aminopolymers," *Jnl of Phy Chem,B, Materials, Surfaces, Interfaces and Biophysical*, Washington DC U.S. v106, No. 6, 2002, pp. 1294-1298; XP002971880, Jan. 18, 2002.
Shim et al (2002) "Functionalization of Carbon Nanotubes for Biocompatibility and Biomolecular Recognition," *Nano Letter*, v2, No. 4, pp. 285-288, Published on Web Jan. 25, 2002.
Shim et al., "Polymer Functionalization for Air-Stable n-Type Carbon Nanotube Field-Effect Transistors," Jnl Am.Chem Soc., v123 pp. 11512-11513, 2001.
Simon (2001) "Micromachined metal Oxide gas sensors: opportunities to improve sensor performance," Sensors and Actuators, v73, pp. 1-26, 2001.
Suri et al. (2002) "Gas and Humidity Sensors Based on Iron Oxide-Polyprrole Nanocomposites," *Sensors and Actuators*, B81, pp. 277-282, 2002.
U.S. Appl. No. 11/318,354 (Gabriel et al.) filed Dec. 23, 2005.
U.S. Appl. No. 11/924,328 (Bryant et al) filed Oct. 25, 2007.

* cited by examiner

REMOTELY COMMUNICATING, BATTERY-POWERED NANOSTRUCTURE SENSOR DEVICES

CROSS-REFERENCE TO RELATED APPLICATIONS

This application claims priority pursuant to 35 U.S.C. § 119(e) to provisional application Ser. No. 60/564,248, filed Apr. 20, 2004, and to provisional application Ser. No. 60/652,883, filed Feb. 15, 2005, which applications are specifically incorporated herein, in their entirety, by reference.

BACKGROUND OF THE INVENTION

1. Field of the Invention

The present invention relates to chemical sensors for remote monitoring, using nanostructures as low-power sensor elements.

2. Description of Related Art

Advances in integrated circuit technology have enabled complex computers to be made small, lightweight, and relatively inexpensively, often as integrated microprocessors. In addition, they can be made to consume relatively small amounts of power. Computers in this class are not as sophisticated as state-of-the-art personal computers, but are powerful enough to process 16-bit data and do floating-point arithmetic. Because they require so little power, they can be used in devices that run on batteries for relatively long periods of time. Thus, for example, they are useful for applications as diverse as burglar alarms and cell phones.

At the same time, modern communications technology enables computers to exchange information wirelessly. Various protocols for radio communication allow data transmitters to use radio spectrum for brief periods of time in limited regions of space. Using such protocols, computers can communicate using weak radio transmitters that transmit and receive in short pulses. This approach minimizes the power requirements of radio communication. As a result, battery-powered devices can transmit data wirelessly to base stations, while remaining in operation for a relatively long period of time without changing or recharging their batteries. Such devices can be used together as a network of remotely located computers.

One important application for a sensor remote network is monitoring of conditions over a wide area. The use of batteries and radio communication eliminates the need to install wires to connect widely deployed monitors. For example, remote battery-powered sensors are known for monitoring electromagnetic radiation along the length of electric power lines, or the monitoring of water quality over a wide area, using distributed optical sensors. However, it is generally believed that a power source is needed to recharge the batteries to maintain such remote sensors operational for sufficiently long periods.

One type of sensor is a chemical sensor, which measures the presence or absence of a chemical species. A variety of chemical sensors are known in the art; for example optical sensors and catalytic bead sensors. Sensors of this type are often relatively inexpensive, sensitive and specific to particular chemicals. However, they are large, and often operate at high temperature, and require large amounts of power. Another type of chemical sensor is a surface acoustic wave detector. These sensors are often smaller and lighter, but they often respond to a range of chemicals rather than to a specific chemical. Yet another type of chemical sensor is a field-asymmetric ion mobility spectrometer. These sensors are often small, but require large amounts of power, and they are relatively expensive. They are often reasonably specific sensors, but often they are not very sensitive. This list is not exhaustive of the known chemical sensors. It is meant to illustrate that the types of sensors differ widely with respect to their size, sensitivity, resolution, specificity, power requirements, cost, and other properties. Most sensors are not appropriate for use in low-cost, battery-powered, remotely communicating devices.

It is desirable, therefore, to provide a remote sensing device with wireless communication capability, that is both compact and inexpensive. It is further desirable to provide a device that can operate for extended periods on a limited power resource.

SUMMARY OF THE INVENTION

The invention provides a wireless sensor device in which a chemical sensing function is performed by electronic devices made with functionalized nanostructures. The functionalized nanostructure sensors are optimized to be low-cost, low-power, small, sensitive, and selective.

Although sensor systems described herein are particularly suitable for efficient operation by battery power, the typically low power consumption of nanosensor devices having aspect of the invention provides embodiments suitable for operation either using conventional power sources used in portable/remote electronics (e.g., battery, solar cell, miniature fuel cell) and/or using alternative energy resources, such as a thermocouple, radio-frequency energy, electrochemical interactions, supercapacitors, energy scavenging mechanisms, or the like, or combinations thereof. The term "power resource" includes both conventional power sources and also such alternative energy resources.

As used herein, a "nanostructure" is any structure which has at least one dimension smaller than 100 nm. Examples include, but are not limited to, multiwalled nanotubes, single-walled nanotubes, carbon nanotubes, carbon onions, semiconductor nanowires, metal nanowires, nanorods, nanocrystals, and nanoparticles. Examples further include the list of nanostructures provided in the patent application Publ. No. 2002/0117659, by Lieber et al., which is herein incorporated in its entirety by reference.

In certain embodiments having aspects of the invention, an electronic device, such as a nanosensor, may comprise at least one nanostructure is disposed on a substrate. In addition, at least two conducting elements are disposed on the substrate, such that each conducting element is in electrical communication with the at least one nanostructure. In some embodiments of the invention, an additional conducting element, referred to as a gate electrode, is provided such that it is not in electrical communication with the at least one nanostructure, but such that there is an electrical capacitance between the gate electrode and the at least one nanostructure.

Alternative embodiments having aspects of the invention may be configured as a nanostucture capacitive sensor. For example, a nanostructure sensor may comprise an assembly including at least a first nanostructure capacitor element disposed spaced-apart from at least a corresponding second capacitor element, the capacitor elements communicating with circuitry to permit measurement of at least a capacitance and/or impedance of the assembly. The nanostructure element (and/or other adjacent elements) may be functionalized to provide a capacitance response to at least an analyte of interest.

Various alternative device structural arrangements may be employed without departing from the spirit of the invention.

For example, an electronic device, such as a nanosensor, may comprise a layered assembly including at least one nanostructure disposed between at least a pair of spaced-apart boundary layers, in which the boundary layers have at least a conductive portion in communication with the nanostructure. In another example, an electronic device, such as a nanosensor, may comprise a generally elongate rod-like assembly including at least one nanostructure disposed between at least a core element and a shell element, the core and shell having at least a conductive portion in communication with the nanostructure.

Examples of nanostructure electronic devices are provided, among other places, in patent application Ser. No. 10/656,898 filed Sep. 5, 2003 entitled "Polymer Recognition Layers For Nanostructure Sensor Devices", and in application Ser. No. 10/704,066, filed Nov. 7, 2003 entitled "Nanotube-Based Electronic Detection Of Biomolecules" (now published as US 2004-0132070), both of which are incorporated herein, in their entirety, by reference.

Conducting elements may be included in communication with circuitry to measure an electrical, magnetic, electrochemical, electromechanical and/or electromagnetic property of the nanostructure sensor. Any suitable property may provide the basis for sensor sensitivity so as to permit detection and/or measurement of at least one sensor signal, for example, electrical resistance, electrical conductance, current, voltage, capacitance, impedance, transistor "on" current, transistor "off" current, transistor hysterisis or phase change, or transistor threshold voltage. Those skilled in the art will appreciate that other properties may also readily be measured by employment of associated circuitry. Accordingly, this list is not meant to be restrictive of the types of properties that can be measured.

For use in distributed networks, the electrical circuit that measures an electrical property must be low-cost and low-power. Preferably, the electrical circuit comprises low-cost, low-voltage integrated circuits. Such circuits generally have limited voltage and current capacities and limited voltage and current sensitivities. As a result, it is preferred for the nanostructure sensors to have electrical resistances and electrical conductances within certain ranges. Preferably, a sensor has a resistance less than 1 M$\Omega$ and greater than 1 $\Omega$. More preferably, a sensor has a resistance less than 100 k$\Omega$ and greater than 10 $\Omega$. Most preferably, a sensor has a resistance less than 20 k$\Omega$ and greater than 100 $\Omega$.

In some embodiments, a nanostructure sensor is a transistor. A transistor has a maximum conductance, which is the greatest conductance measured with the gate voltage in a range, and a minimum conductance, which is the least conductance measured with the gate voltage in a range. A transistor has an on-off ratio, which is the ratio between the maximum conductance and the minimum conductance. To make a sensitive chemical sensors, a nanostructure transistor has an on-off ratio preferably greater than 1.2, more preferably greater than 2, and most preferably greater than 10. For example, a nanostructure electronic device, without the functionalization that converts the device to a sensor, may exhibit relatively high conductance at gate voltages less than about −5 V and relatively low conductance at gate voltages greater than about 0 V.

In a preferred embodiment of the invention, nanostructure electronic devices are optimized to have resistances within the preferred range of resistance and on-off ratios within the preferred range of on-off ratio. Many nanostructures are disposed on the substrate, all of them being in electrical communication with the conducting elements. In some embodiments, the many nanostructures are nanowires or nanotubes that are oriented substantially parallel. In some embodiments, the many nanostructures are nanowires or nanotubes that are oriented randomly. Methods for disposing many nanostructures are disclosed in patent application Ser. No. 10/177,929, filed Jun. 21, 2002 by Gabriel et al., which is herein incorporated by reference, in its entirety. Myriad paths are available for electrical current to flow between the conducting elements through the nanostructures. In some embodiments, each current path includes only one nanostructure; in other embodiments, each current path includes at least two nanostructures in series. The number of nanostructures, the number of current paths, and the number of nanostructures in series in a current path may be chosen to provide resistance and on-off ratio within the preferred ranges.

The nanostructure sensors utilize nanostructures which have been functionalized, which means treated with one or more recognition materials. A recognition material is a substance which is disposed on the substrate in the immediate vicinity of the at least one nanostructure or directly on the at least one nanostructure, such that the nanostructure electronic device responds electrically to a change in the concentration of a chemical species. Examples of sensing agents are provided in Publ. No. 2002/0117659 referenced hereinabove, in provisional patent application Ser. No. 60/502,485, filed Sep. 12, 2003 by Star et al., and International Application No. PCT/US04/30,136 entitled "Carbon dioxide nanoelectronic sensor", published as WO05/026,694 on Mar. 24, 2005, each of which references are herein incorporated, in their entirety, by reference. Other suitable sensing agents may also be used, as known in the art.

Functionalized nanostructure sensors are able to detect chemical species with high selectivity and high sensitivity. Furthermore, they require low amounts of power to operate. To use them in remote networked sensor devices, they should be integrated with further circuitry. The invention provides circuitry which measures an electrical property of the nanostructure sensor. An electrical property includes, but is not limited to, electrical resistance, capacitance, transistor threshold voltage, electrical current, and transistor off current. The circuitry which measures an electrical property may comprise a microprocessor, of which many examples are known in the art. In some embodiments, the circuitry further comprises an analog-to-digital converter. In some embodiments, the circuitry further comprises a regulated voltage source. The microprocessor, analog-to-digital converter, and regulated voltage source should be chosen such that they require low amounts of electrical power and such that they are low in cost.

A remotely communicating sensor device according to the invention comprises at least one functionalized nanostructure sensor, electrical circuits to measure the at least one sensor, and a communications circuit. The communications circuit comprises an antenna configured to transmit and receive radio waves and a circuit configured to control the antenna. Many examples of wireless communications circuits are known in the art, and any suitable low-power circuit may be employed. The invention is intended to be practiced with any radio communications circuit with low power requirements, for example, a circuit appropriate for extended operation in a remote battery-powered device without need for recharging.

It should be understood that, while a nanosensor may be fabricated as a discrete sensor device or sensor array, alternatively various additional components of a nanosensor apparatus having aspects of the invention may be integrated on a single "chip" or other base material (e.g., a flexible substrate), without departing from the spirit of the invention. For example additional components such as electronic circuitry, signal processors, memory devices, logic devices, photocells, optical elements, microfluidic elements, and the like may be integrated on a chip which includes one or more nanosensor devices in operative communication one or more such additional components. The integrated chip may be fabricated using techniques commonly employed for electronic integrated circuits (IC), microfluidic devices, and the like.

In some embodiments, a remotely communicating sensor device transmits data from a nanostructure sensor to a base station. An example of this embodiment is provided in Example A. It should be understood that remotely communicating sensor systems having aspects of the invention may include a range of alternative remote communication architectures, in addition to a remote sensor-base station embodiment. In some embodiments, multiple remotely communicating devices transmit and receive data from each other, forming a network of devices. To conserve power, in some embodiments a remote sensor may be made to transmit sensing data only intermittently, for example, at predetermined intervals or when queried by a base station or other compatible device. Some embodiments may include a plurality intercommunicating remote sensor units which may provide multiple transmission paths (e.g. for robustness), repeater station capability (e.g., for increased range with low power consumption), distributed processing, and the like.

A more complete understanding of the nanostructure sensor devices will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

The present invention provides a remotely communicating, low-power nanostructure sensor. The sensor is capable of operating for long periods on a limited power source, such as a small battery. In the alternative, the sensor may be powered by other low-power sources. Exemplary embodiments are described below. In the detailed description that follows, like element numerals are used to denote like elements appearing in one or more of the figures.

The remotely communicating sensor may incorporate a nanosensor comprising a nanostructure functionalized to respond to the presence of a chemical or compound. The nanosensor may be configured as a field effect transistor (FET) device, wherein the conductivity of the sensor depends on the value of an applied gate voltage, and on chemicals in the surrounding environment of the nanosensor. A nanotube may be used as a nanostructure conducting channel in a FET; such a device may be referred to as a NTFET. An exemplary architecture for a nanosensor for use with the invention is described below.

1. Nanosensor Architecture

Figure 1:
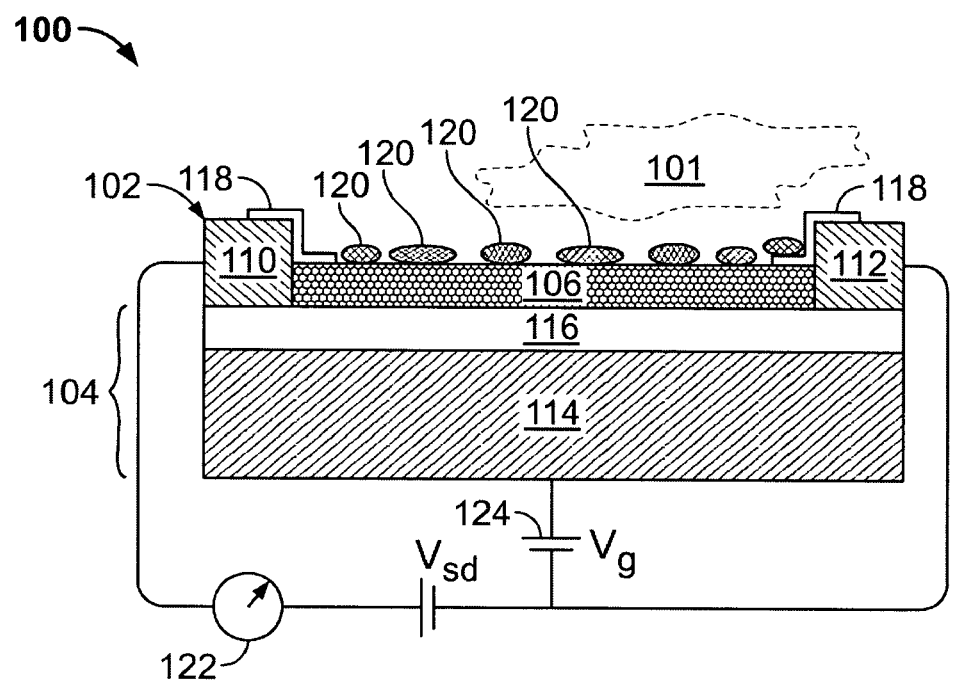
FIG. 1 is a schematic diagram showing an exemplary nanosensor and associated circuit elements for a remote sensing device.

FIG. 1. shows an electronic sensing device 100 for detecting an analyte 101 (e.g. hydrogen gas), comprising a nanostructure sensor 102. Sensor 102 comprises a substrate 104, and a conducting channel or layer 106 comprising a nanostructure material, such as a nanotube or network of nanotubes, disposed on the substrate.

The nanostructure material 106 may contact the substrate as shown, or in the alternative, may be spaced a distance away from the substrate, with or without a layer of intervening material. In an embodiment of the invention, conducting channel 106 may comprise one or more carbon nanotubes. For example, conducting channel 106 may comprise a plurality of nanotubes forming a mesh, film or network.

At least two conductive elements or contacts 110, 112 may be disposed over the substrate and electrically connected to conducting channel 106 comprising a nanostructure material. Elements 110, 112 may comprise metal electrodes in direct contact with conducting channel 106. In the alternative, a conductive or semi-conducting material (not shown) may be interposed between contacts 110, 112 and conducting channel 106. Contacts 110, 112 may comprise source and drain electrodes, respectively, upon application of a source-drain voltage $V_{sd}$. The voltage or polarity of source 110 relative to drain 112 may be variable, e.g., the applied voltage may be DC, AC, pulsed, or variable. In an embodiment of the invention, the applied voltage is a DC voltage.

Device 100 may be operated as a gate-controlled field effect transistor, with sensor 102 further comprising a gate electrode 114. Gate 114 may comprise a base portion of substrate 104, such as a doped-silicon wafer material isolated from contacts 110, 112 and channel 106 by a dielectric layer 116, so as to permit a capacitance to be created by an applied gate voltage $V_g$. For example, the substrate 104 may comprise a silicon back gate 114, isolated by a dielectric layer 116 comprising $SiO_2$.

Sensor 102 may further comprise a layer of inhibiting or passivation material 118 covering regions adjacent to the connections between the conductive elements 110, 112 and conducting channel 106. The inhibiting material may be impermeable to at least one chemical species, such as to the analyte 101 or to environmental materials such as water or other solvents, oxygen, nitrogen, and the like. The inhibiting material 118 may comprise a passivation material as known in the art, such as silicon dioxide, aluminum oxide, silicon nitride, or other suitable material. Further details concerning the use of inhibiting materials in a NTFET are described in prior application Ser. No. 10/280,265, filed Oct. 26, 2002, entitled "Sensitivity Control For Nanotube Sensors" (published as US 2004-0043527 on Mar. 4, 2004) which is incorporated by reference herein.

The conducting channel 106 (e.g., a carbon nanotube layer) may be functionalized to produce a sensitivity to one or more target analytes 101. Although nanostructures such as carbon nanotubes may respond to a target analyte through charge transfer or other interaction between the device and the analyte, more generally a specific sensitivity can be achieved by employing a recognition material 120, also called a functionalization material, that induces a measurable change in the device characteristics upon interaction with a target analyte. The sensor functionalization material 120 may be selected for a specific application, such as to interact with a targeted analyte 101 to cause a measurable change in electrical properties of nanosensor device 102. For example, the functionalization material 120 may cause an electron transfer to occur in the presence of analyte 101, or may influence local environment properties, such as pH and the like, so as to indirectly change device characteristics. Alternatively or additionally, the recognition material may induce electrically-measurable mechanical stresses or shape changes in the nanostructure channel 106 upon interaction with a target analyte.

Sensitivity to an analyte or to multiple analytes may be provided or regulated by the association of a nanotube conducting channel 106 with an adjacent functionalization material 120. Specific examples of suitable functionalization materials are provided later in the specification. The functionalization material 120 may be disposed as a continuous or discontinuous layer on or adjacent to channel 106.

Device 100 may further comprise suitable circuitry in communication with sensor elements to perform electrical measurements. For example, a conventional power source may supply a source drain voltage $V_{sd}$ between contacts 110, 112. Measurements via the sensor device 100 may be carried out by circuitry represented schematically by meter 122 connected between contacts 110, 112. In embodiments including a gate electrode 114, a conventional power source 124 may be connected to provide a selected or controllable gate voltage $V_g$. Device 100 may include one or more electrical supplies and/or a signal control and processing unit (not shown) as known in the art, in communication with the sensor 102.

Optionally, device 100 may comprise a plurality of sensors like sensor 102 disposed in a pattern or array, such as described in prior application Ser. No. 10/388,701 filed Mar. 14, 2003 entitled "Modification Of Selectivity For Sensing For Nanostructure Device Arrays" (now published as US 2003-0175161), which is incorporated by reference herein. Each device in the array may be functionalized with identical or different functionalization. Identical device in an array can be useful in order to multiplex the measurement to improve the signal/noise ratio or increase the robustness of the device by making redundancy. Different functionalization may be useful for providing sensitivity to a greater variety of analytes with a single device.

2. Sensor Elements

Substrate. The substrate 104 may be insulating, or on the alternative, may comprise a layered structure, having a base 114 and a separate dielectric layer 116 disposed to isolate the contacts 110, 112 and channel 106 from the substrate base 114. The substrate 104 may comprise a rigid or flexible material, which may be conducting, semiconducting or dielectric. Substrate 104 may comprise a monolithic structure, or a multilayer or other composite structure having constituents of different properties and compositions. Suitable substrate materials may include quartz, alumina, polycrystalline silicon, III-V semiconductor compounds, and other suitable materials.

Substrate materials may be selected to have particular useful properties, such as transparency, microporosity, magnetic properties, monocrystalline properties, polycrystalline or amorphous properties, or various combinations of these and other desired properties. For example, in an embodiment of the invention, the substrate 104 may comprise a silicon wafer doped so as to function as a back gate electrode 114. The wafer being coated with intermediate diffusion barrier of $Si_3N_4$ and an upper dielectric layer of $SiO_2$. Optionally, additional electronic elements may be integrated into the substrate for various purposes, such as thermistors, heating elements, integrated circuit elements or other elements.

In certain alternative embodiments, the substrate may comprise a flexible insulating polymer, optionally having an underlying gate conductor (such as a flexible conductive polymer composition), as described in application Ser. No. 10/846,072 filed May 14, 2004 entitled "Flexible Nanotube Transistors", the entirety of which application is incorporated herein by this reference.

In further alternative embodiments, the substrate may comprise a microporous material permitting suction to be applied across the substrate, e.g., porous alumina for vacuum deposition of a nanotube network channel 106 from suspension or solution, as described in application Ser. No. 60/639,954, filed Dec. 28, 2004, entitled "Nanotube Network-On-Top Architecture For Biosensor", the entirety of which application is incorporated herein by reference.

Contacts. The conductor or contacts 110, 112 used for the source and drain electrodes can be any of the conventional metals used in semiconductor industry, or may be selected from Au, Pd, Pt, Cr, Ni, ITO, W or other metallic material or alloy or mixture thereof. In the alternative, the contact may comprise a multi-layer or composite of metallic materials, such as Ti+Au, Cr+Au, Ti+Pd, Cr+Pd, or the like. A multilayer construction may help in improving the adhesion of the metal to the substrate. For example, electrical leads may be patterned on top of a nanotube network channel from titanium films 30 nm thick capped with a gold layer 120 nm thick. In the alternative, other conductive materials may be employed, such as conductive polymers and the like.

The dimension of the distance between source 110 and drain 112 may be selected to achieve desired characteristics for a particular application. It should be understood that one or more of each of a source and drain electrode may be arranged in an interdigitated or spaced-apart electrode array, permitting a comparative large area of nanostructure channel 106 having a comparatively small source-drain gap to be arranged compactly.

Gate electrode 114 may comprise materials generally similar to contacts 110, 112. In the alternative, the gate electrode 114 may comprise a sublayer within substrate 104. Gate electrode 114 may comprise doped silicon, patterned metal, ITO, other conductive metal or non-metal material, or combinations thereof. Alternative forms of gate electrodes may be employed, such as a top gate, a gate effected via a conducting analyte carrier medium (e.g. an aqueous solution). Optionally, a device 102 may comprise such other electrodes as a counter electrode, a reference electrode, a pseudo-reference electrode, without departing from the spirit of the invention.

Conducting Channel Or Nanostructure Layer. Exemplary embodiments having aspects of the invention include sensor devices having at least one conducting channel 106 comprising one or more nanostructures. For example, conducting channel or layer 106 may comprise one or more single-wall carbon nanotubes, multiple-wall carbon nanotubes, nanowires, nanofibers, nanorods, nanospheres, or other suitable nanostructures. In addition, or in the alternative, conducting channel or layer 106 may comprise one or more nanostructures comprised of boron, boron nitride, and carbon boron nitride, silicon, germanium, gallium nitride, zinc oxide, indium phosphide, molybdenum disulphide, silver, or other suitable materials. Various suitable methods for manufacturing nanotubes and other nanostructures are known in the art, and any suitable method may be used.

Conducting Channel Comprising A Nanostructure Network. In an embodiment of the invention, conducting channel or nanostructure layer 106 comprises an interconnected network of smaller nanostructures disposed to form a percolation layer, mesh, or film which provides at least one electrical conduction path between a source electrode 110 and a drain electrode 112. In such a network of nanoparticles, it is not necessary that any single nanoparticle extends entirely between the source and drain contacts. In operation the conductivity of channel 106 between source electrode 110 and drain electrode 112 may be maintained by interconnections, contacts or communications between adjacent nanostructures. Such networks of nanoparticles, such as nanotubes and the like, may be configured to be defect-tolerant, in that disruption of any particular conductive path may be compensated by remaining paths within the network.

In an embodiment of the invention, nanostructure conducting channel 106 comprises one or more single-walled or multi-walled carbon nanotubes. The nanotubes may be arranged as clumps or bundles, or as distinct separated fibers. A useful network of nanotubes may be provided, for example, by distributing a dispersion of nanotubes over a substrate so as to be approximately planar and randomly oriented. For example, conducting channel 106 may comprise a network including a plurality of dispersed single wall carbon nanotubes (SWCNT), in which the nanotubes are oriented substantially randomly, non-parallel and separated with respect to one another (i.e., not clumped) as an interconnecting mesh disposed generally parallel to the substrate.

Electrical characteristics of the channel 106 may be optimized to suit a particular functionalization chemistry or other constituent of the sensor which effects conductivity, or to suit a desired range of analyte concentration. In preferred embodiments, the density or thickness of a nanotube network may be varied to provide a desired degree of conductivity between the source and drain electrodes. In the alternative, or in addition, the proportion of metallic or semiconducting nanotubes in the network may be selected to achieve a desired conductivity in the network. One advantage of using a nanostructure network architecture for the conducting channel 106 is that these factors may be varied to produce a conducting network having a selected margin above (or below) the percolation limit, permitting convenient optimization of device characteristics. For example, a NT network channel may be formed to be slightly below the percolation limit for the uncoated network, and modified by deposition of a conducting recognition material, such as Pd, to result in a functionalized channel of desired conductivity. In another example, the conductivity of an initially dry network may be selected to allow for operation in association with anticipated additional conductivity of a fluid analyte medium, such as a physiologic buffer or solvent.

In addition, a conducting channel 106 comprising a generally random dispersion of individual nanoparticles advantageously permits a "statistical," rather than a "localized" approach to nanostructure device fabrication, which may be more amenable to demanding mass production techniques. In the "statistical" approach, electrical contacts can be placed anywhere on the dispersion of individual nanostructures to form devices, without a specific correspondence between electrode position and any particular nanoparticle position. The random dispersion of nanoparticles ensures that any two or more electrodes placed thereon can form a complete electrical circuit with functioning nanostructures providing the connection. By distributing a large plurality of randomly oriented nanotubes in a dispersion over (or under) an electrode array, uniform electrical properties in the individual devices can be assured with higher yields and faster processing than is possible using the prior art approach of controlled placement or growth of individual nanotubes or other nanostructures.

Nanoparticle Network Formation. Suitable nanostructure networks may be formed by various suitable methods. One suitable approach may comprise forming an interconnecting network of single-wall carbon nanotubes directly upon the substrate, such as by reacting vapors in the presence of a catalyst or growth promoter disposed upon the substrate. For example, single-walled nanotube networks can be grown on silicon or other substrates by chemical vapor deposition from iron-containing catalyst nanoparticles with methane/hydrogen gas mixture at about 900 degree C. Other catalyst materials and gas mixtures can be used to grow nanotubes on substrates, and other electrode materials and nanostructure configurations and are disclosed in application Ser. No. 10/099,664, filed Mar. 15, 2002 entitled "Modification Of Selectivity For Sensing For Nanostructure Sensing Device Arrays", and in International Application No. PCT/US03/19, 808, filed Jun. 20, 2003, entitled "Dispersed Growth Of Nanotubes On A Substrate" and published as WO2004-040, 671, both of which applications are incorporated by reference herein.

Advantageously, the use of highly dispersed catalyst or growth-promoter for nanostructures permits a network of nanotubes of controlled diameter and wall structure to be formed in a substantially random and unclumped orientation with respect to one another, distributed substantially evenly at a selected mean density over a selected portion of the substrate. The particle size distribution may be selected to promote the growth of particular nanotube characteristics, such as tube diameter, number of walls (single or multi-walled), conductivity, or other characteristics.

In the alternative, conducting layer 106 comprising an interconnecting network of nanostructures may be formed by deposition from a solution or suspension of nanostructures, such as a solution of dispersed carbon nanotubes. See for example, the methods described in the above incorporated application Ser. No. 10/846,072, filed May 14, 2004 entitled "Flexible Nanotube Transistors". Such methods as spin coating, spray deposition, dip coating and ink-jet printing may be employed to deposit the solution or suspension of nanostructures.

Yet another suitable approach may comprise forming a nanotube network by suction deposition on a porous substrate or membrane, as described in application Ser. No. 60/639, 954, filed Dec. 28, 2004, entitled "Nanotube Network-On-Top Architecture For Biosensor", which application is incorporated herein, in its entirety, by reference. The network thus formed may be used as a conducting channel either attached to its deposition membrane, or after being separated from the deposition membrane using a method such as membrane dissolution or transfer bonding.

Carbon nanotubes are known to exhibit either metallic or semiconductor properties, depending on the particular graphitic lattice orientation. Various methods may be employed to select a desired composition of nanotubes for a nanostructure layer 106 of a nanosensor device 102. For example, a plurality of generally similar nanotube devices may be fabricated in a parallel mass production process, such as an array of device dies disposed on a silicon wafer. Each of the plurality of devices will exhibit an electrical characteristic with a statistically predictable range of characteristics, due to differing metallic or semiconductor composition of each devices conducting layer 106. The fabricated dies may be individually tested, such as by automated or semi-automated pin probe test rigs. Dies exhibiting a selected electrical behavior or range of behavior may be marked and selected for further processing and use, and any non-conforming dies may be culled, or otherwise processed for other uses.

In the alternative, a network of nanostructures for conducting channel 106 may be constructed from preprocessed source nanotube material which includes a selected composition of metallic versus semiconductor properties (e.g., solely semiconductor nanotubes). Alternatively, the nanotube layer may be formed of an arbitrary mixture of nanotube composition, and the layer subsequently treated to selectively remove, oxidize, disconnect or deactivate all or a portion of the metallic nanotubes, e.g. by ohmic heating, so as to leave a conducting channel of selected properties (e.g., solely semiconductor nanotubes). The latter approach may be employed advantageously where the nanotube layer 2 is formed directly upon the substrate 1, for example by catalyst initiated CVD.

Functionalization or Recognition Layer. Functionalization material 120 may be selected for a wide range of alternative chemical or biomolecular analytes. Examples include functionalization specific to gas analytes of industrial or medical importance, such as carbon dioxide as disclosed in application Ser. No. 10/940,324 filed Sep. 13, 2004 entitled "Carbon Dioxide Nanoelectronic Sensor", which is incorporated herein by reference. See also application Ser. No. 10/656,898 referenced hereinabove.

Examples of functionalization materials specific to biomolecules, organisms, cell surface groups, biochemical species, and the like are disclosed in application Ser. No. 10/345,783, filed Jan. 16, 2003, entitled "Electronic Sensing Of Biological And Chemical Agents Using Functionalized Nanostructures" (now published as US 2003-0134433), and in application Ser. No. 10/704,066 referenced hereinabove, both of which applications are incorporated herein by reference.

Functionalization material 120 may comprise as little as a single compound, element, or molecule bonded to or adjacent to the nanostructure channel 106. In addition, or in the alternative, functionalization materials may comprise a mixture or multilayer assembly, or a complex species (e.g., including both synthetic components and naturally occurring biomaterials). Further examples and more detailed disclosures regarding functionalization materials are disclosed in application Ser. No. 10/388,701, filed Mar. 14, 2003 entitled "Modification Of Selectivity For Sensing For Nanostructure Device Arrays" (published as US 2003-0175161), and in application Ser. No. 60/604,293, filed Nov. 19, 2004, entitled "Nanotube Sensor Devices For DNA Detection", which applications are incorporated herein by reference.

Functionalization material 120 and other sensor elements may be selected to suit various physical forms of sample media, such as gaseous or liquid analyte media. See, for example, application Ser. No. 10/773,631, filed Feb. 6, 2004 entitled "Analyte Detection In Liquids With Carbon Nanotube Field Effect Transmission Devices", and application Ser. No. 60/604,293, filed Nov. 13, 2004, entitled "Nanotube Based Glucose Sensing," both of which applications are incorporated herein by reference.

Functionalization of an H2 Sensor Embodiment. In an exemplary embodiment of an $H_2$ sensor, the functionalization material 120 may comprise metal particles and/or larger aggregates. For example, the functionalization material 120 may comprise a metal which has a catalytic or other interaction with hydrogen, such as Pd, Pt, Au, Ni, Ti, or alloys or combinations thereof. In an embodiment of a hydrogen sensor, the functionalization material may comprise Pd, either alone or as an alloy. For example, an alloy such as Pd/Ni 90/10% w/w or Pd/Ti 90/10% w/w may be used; one particularly useful alloy may comprise Pd and about 16.3% w/w of Ni. Alloys of Pd with other metals may also be employed, for example Pd/Au, Pd/V, Pd/Cu. Palladium and other metals may be evaporated on the sensor 102 to provide a functionalization layer 120 on or adjacent to the conducting channel 106.

In addition, or in the alternative, metals may be electrodeposited specifically on the nanostructure channel 102, as described in more detail in application Ser. No. 10/945,803, filed Sep. 20, 2004 entitled "Multiple Nanoparticles Electrodeposited On Nanostructures," which is incorporated by reference herein, and in the above referenced application Ser. No. 10/388,701. The described methods of electrodeposition from solution (e.g. $PdCl_2$) permit control of the particle size and particle distribution density within selected limits, and also permit selected target structures on a device to be coated with metal particles, while avoiding deposition on adjacent structures.

In certain embodiments of sensors having aspects of the invention, the functionalization material may be distributed more or less uniformly over the device surface. In the alternative, there may be advantages to a selective distribution of functionalization material. For example, in an exemplary embodiment of a hydrogen sensor, a functionalization metal such as a Pd or a Pd alloy may be deposited so as to only partially cover the nanotube layer, so that the functionalization metal is not substantially in contact with either the source or drain electrodes 110, 112. For example, in certain embodiments, Pd or a Pd alloy may be deposited by evaporation so that a plurality of small fields are created, called "bars".

Patterning of deposition of functionalization materials and other elements of sensor 102 may employ photolithographic and masking technology such as used industrially for the making of integrated circuits. Alternatively, for appropriate feature sizes, shadow masking, ink-jet printing other patterning techniques may be employed for selective application of functionalization and other materials. Using any suitable deposition method, sensor-specific functionalization, passivation or encapsulation materials may be applied in a plurality of different patterns to selected portions of an array of sensors, so as to produce a multifunctional sensor array.

By leaving a portion of nanostructures 106 exposed, i.e., not covered with metal, the electrical field created at the gate electrode may be modulated in a selected fashion by the functionalization metal. This may permit more functionalization metal to be incorporated in a device of a given size without an undesirable degree of screening, thereby enhancing the device response to the analyte (e.g. hydrogen). In addition, using more functionalization metal may extend the useful lifetime of the device, particularly where oxidative or other decay of the functionalization metal is a life-limiting factor.

An additional advantage of the use of selective functionalization metal deposition (such as Pd "bars") is to increase the dynamic range of the sensor device or sensor array system. In one exemplary embodiment the concentration of a relatively thick layer of functionalization metal in the bar gives a broader $H_2$ concentration response range than a thin continuous functionalization metal coating which reaches saturation over a narrow range. In an alternative embodiment, an array of generally similar sensor devices having a range of different sizes or number of bars may be provided, with different sensors responding most sensitively to a different range of $H_2$ concentration.

In the alternative, or in addition, a layer of passivation material may be deposited over nanostructure channel 106 prior to deposition of the functionalization material, to separate the functionalization material from the channel. For example, a layer of $SiO_2$ may be deposited covering all or a portion of the nanotube network, followed by the deposition of a Pd or other functionalization material on top of the $SiO_2$ layer. The dielectric layer may permit greater response of the sensor to variation in gate electrode voltage (e.g., a substrate gate electrode). In the alternative, a conductive functionalization material in this configuration may serve as a gate electrode. For example, a layer of Pd functionalization metal or alloy separated from an NT network channel by a dielectric layer may be connected to an electrical lead, so as to permit a gate voltage to be applied to the functionalization material.

Functionalization of an CO2 Sensor Embodiment. In an exemplary embodiment of an $CO_2$ sensor, sensitivity to $CO_2$ may be achieved using a suitable functionalization layer 120. The functionalization layer should perform two main functions: 1) it should selectively recognize carbon dioxide molecules and 2) upon the binding of $CO_2$ it should generate an amplified signal that is transferred to the carbon nanotube transducer. In the presence of water, carbon dioxide forms carbonic acid which dissociates and alters the pH of the functionalization layer, thus protonating the electron donating groups and making the NTFET more p-type. Basic inorganic compounds (e.g., sodium carbonate), pH-sensitive polymers, such as polyaniline, poly(ethyleneimine), poly(o-phenylenediamine), poly(3-methylthiophene), and polypyrrole, as well as aromatic compounds (benzylamine, naphthalenemethylamine, antracene amine, pyrene amine, etc.) may be used to functionalize NTFETs for $CO_2$ sensing. The functionalization layer may be constructed using certain polymeric materials such as polyethylene glycol, poly(vinyl alcohol) and polysaccharides, including various starches as well as their components amylose and amylopectin.

Materials in the functionalization layer may be deposited on the NTFET using various different methods, depending on the material to be deposited. For example, inorganic materials, such as sodium carbonate, may be deposited by drop casting from 1 mM solution in light alcohols. The functionalized sensor may then be dried by blowing with nitrogen or other suitable drying agent. Polymeric materials may be deposited by dip coating. A typical procedure may involve soaking of the chip with the carbon nanotube device in 10% polymeric solution in water for 24 hours, rinsing with water several times, and blowing the chip dry with nitrogen. Polymers which are not soluble in aqueous solutions may be spin coated on the chip from their solutions in organic solvents. Values of polymer concentrations and the spin coater's rotation speeds may be optimized for each polymer.

Further aspects of a nanosensor for sensing carbon dioxide are disclosed in application Ser. No. 10/940,324 filed Sep. 13, 2004 entitled "Carbon Dioxide Nanoelectronic Sensor," which is incorporated herein, in its entirety, by reference.

3. Sensor Arrays

A plurality of sensor devices 102 may be conveniently arranged as an array embodiment, the array being configured to provide for a number of advantageous measurement alternatives, as described in the patent applications incorporated by reference above. A number of different measurement methods and benefits are enabled by a sensor array according to the invention, for example:

a) multiple analytes detected by a plurality of specifically functionalized sensors, b) increased precision and dynamic range by a plurality of sensors each of which is optimized for a different range, c) increased analyte specificity and flexibility by detecting a characteristic "profile" of responses of a selected target analyte to a plurality of differently-functionalized sensors, d) self calibration systems and isolated reference sensors, e) multiple use array having a plurality of addressable one-time-use sensor sub-units, or f). ultra-low-cost direct-digital-output sensor arrays, including a plurality of sensors, each producing a binary signal, and collectively having a range of response thresholds covering a selected analyte concentration range.

4. Measurement Systems

The electronic circuitry described in this example is by way of illustration, and a wide range of alternative measurement circuits may be employed without departing from the spirit of the invention.

Embodiments of an electronic sensor device having aspects of the invention may include an electrical circuit configured to measure one or more properties of the nanosensor 120, such as measuring an electrical property via the conducting elements 110, 112. Any suitable electrical property may provide the basis for sensor sensitivity, for example, electrical resistance, electrical conductance, current, voltage, capacitance, transistor on current, transistor off current, and/or transistor threshold voltage. In the alternative, or in addition, sensitivity may be based on a measurements including a combination of properties, relationships between different properties, or the variation of one or more properties over time.

For example, a transistor sensor may be controllably scanned through a selected range of gate voltages, the voltages compared to corresponding measured sensor current flow (generally referred to herein as an $I$-$V_g$ curve or scan). Such an $I$-$V_g$ scan may be through any selected gate voltage range and at one or more selected source-drain potentials. The $V_g$ range is typically selected from at least device "on" voltage through at least the device "off" voltage. The scan can be either with increasing $V_g$, decreasing $V_g$, or both, and may be cycled positive or negative at any selected frequency.

From such measurements, and from derived properties such as hysteresis, time constants, phase shifts, or scan rate/frequency dependence, correlations may be determined with target detection or concentration. The electronic sensor device may include or be coupled with a suitable microprocessor or other computer device as known in the art, which may be suitably programmed to carry out the measurement methods and analyze the resultant signals. Those skilled in the art will appreciate that other electrical or magnetic properties may also be measured as a basis for sensitivity. Accordingly, the embodiments disclosed herein are not meant to restrict the types of device properties that can be measured.

Temperature and Pressure Compensation. Optionally, measurement precision and accuracy may be enhanced by use of compensation methods, for example, multiple linear regression (MLR) for temperature and humidity. A similar approach may be used with pressure instead of relative humidity. The compensation method may include electrical measurements of the sensor, such as resistance, polynomial terms to account for nonlinearity, temperature and pressure measurements, and interactions. For example, a relation of temperature and resistance may be used to account for change of sensitivity with temperature, as follows:

$$C=k_0+k_1R+k_2T+k_3RT+\epsilon$$

where C is gas concentration, R is sensor resistance, T is temperature and $\epsilon$ is regression error.

Calibration data may be generated using a classic full factorial experimental design. The factors for such calibration may include analyte gas concentration, temperature, pressure and relative humidity. The levels may be balanced in such a way that any sensor drift will not be confused with responses to such factors or interactions of factors. Collected data may be stored in a relational database, and MLR performed on the stored data. The resulting coefficients and goodness-of-fit statistics may also be stored in a database. These coefficients can be applied to data from other tests for validation, or programmed into the sensor system firmware. Principal component analysis (PCA) may be performed on test data, to makes it possible to represent multivariate data in fewer dimensions. Temperature sensors, such as a thermistor may be included in the sensor system to permit automatic electronic compensation for the variation of temperature. Software or firmware for performing these and other calculations using nanosensor inputs may be held in a memory of a remote sensor device, for execution by a remote processor of a device 100.

5. Substrate Protective Structures

In an embodiment of the invention, a nanosensor may comprise a substrate that is sensitive to contamination occurring during fabrication steps or from other environmental exposure. For example, a semiconductor substrate such as a silicon wafer may be used. It is desired that the electrical properties of the base portion of the wafer or dielectric coating be carefully controlled during processing to achieve desired insulating, semiconducting or conducting properties in the completed sensor structure.

Figure 2:
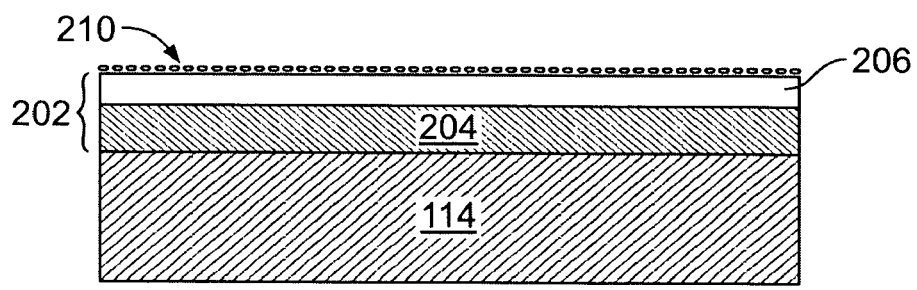
FIG. 2 is a schematic diagram showing a side view of a substrate for preparing an exemplary nanosensor device.
Figure 3A:
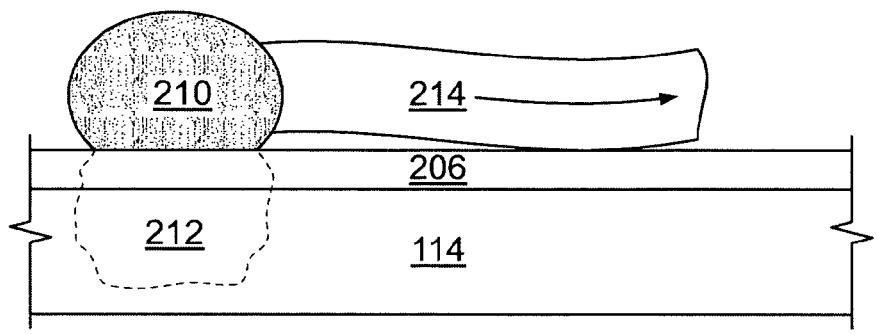
FIGS. 3A-B are schematic diagrams showing a side view of a substrate growing a nanotube from a catalyst particle, which illustrate the effect of a diffusion barrier.
Figure 3B:
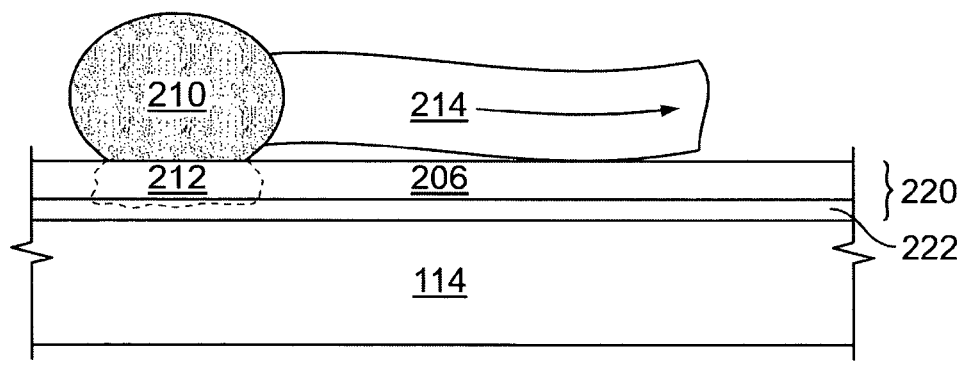

As shown schematically in FIGS. 2 and 3B, in an embodiment of the invention a substrate 114 for a nanosensor device like device 102 may be provided with a novel substrate protective structure or layer 202, comprising a diffusion barrier 204 protecting the substrate 114. The diffusion barrier 202 should function to protect the underlying substrate 114 so as to prevent contamination such as might occur during fabrication of sensor devices on the substrate. For example, fabrication of sensor devices may involve placing a metal catalyst or other growth promoter 210 (e.g., iron or iron oxide) on a substrate to initiate growth of nanotubes by chemical vapor deposition (CVD)), as known in the art. When growing nanoparticles by CVD, a combination of high temperatures and reducing atmosphere are commonly used. As a consequence of these conditions, element migration or diffusion of metals is greatly increased.

Contaminant Migration. FIG. 3A shows a schematic view of a substrate 114 supporting a growing nanotube 214 from a catalyst particle 210, such as may occur during a CVD process. Without the presence of a diffusion barrier, under CVD processing conditions a metal (e.g., iron) or other material may migrate from a catalyst particle 210 through a dielectric layer 206 (e.g. $SiO_2$) to contaminate the underlying substrate 114 in a "poisoned region" 212, so as to degrade the characteristics of the silicon substrate or dielectric layer. Such contamination may create a shorting conduction path from a nanostructure channel or from contacts through the dielectric 206 to gate electrode 114, so as to bleed off the capacitance of the gate electrode, divert source-drain current, or degrade transistor on/off ratio.

It may be desirable, therefore, to limit migration of catalyst into the substrate by increasing the thickness of the layer of $SiO_2$ so that metals do not have the time to migrate through the whole layer during the exposure to elevated temperatures. However, this may lead to very thick dielectric layers, such as more than about 500 nm. For efficient gate operation, it may be desirable to keep the thickness of the dielectric layer above the gate electrode as low as possible, or at any rate much less than 500 nm, to keep functional gate voltages as low as possible. To this end, a diffusion barrier may be provided under the dielectric layer 206, as described below.

Diffusion Barrier. As shown in FIG. 3B, in an embodiment of the invention, a diffusion barrier or contaminant protective layer 220 may be provided between substrate 114 and contaminants in the environment, such as catalyst particles. During fabrication of nanotubes or other nanostructures on substrate 114, layer 220 may operate to chemically isolate nanostructure catalyst materials 210 from diffusing into the substrate material. In the illustrated embodiment, the contaminated region created by diffusion during CVD processing does not penetrate into base material 114. In an embodiment of the invention, a suitable diffusion barrier 220 comprises a layer of $Si_3N_4$ 222 from about 50 to about 3000 nm thick, and more preferably from about 50 to about 1000 nm thick. A suitable layer may be formed by methods known in the art, such as by CVD, EPCVD, or other suitable method. A layer of $Si_3N_4$ is more resistant to the diffusion of growth promoter elements than a comparable layer of $SiO_2$. In addition, the larger dielectric constant of $Si_3N_4$ also favors low gate voltages. Other materials may also be useful for creating a diffusion barrier more effective than $SiO_2$.

Conditioned Surface Layer. Diffusion barrier 220 may further comprise a conditioned surface layer 206 overlying a diffusion blocking layer 222, such as a $Si_3N_4$ layer. Oftentimes, specific surface characteristics, chemical properties or morphology are desired for the substrate. For example, it may be desired to have a conditioned surface layer with characteristics selected to promote attachment or uniform dispersal of a functionalization material. In addition, when a nanosensor is to be fabricated by growing a nanotube 214 or other nanostructure on the substrate, surface characteristics may influence the rate of nanostructure growth or properties of the resulting nanostructures, for example, a population density or length of nanotubes. Although a diffusion barrier such as a $Si_3N_4$ layer may be used as a surface layer alone to protect the bulk silicon substrate, such a layer may be less favorable to nanotube growth than a surface layer of $SiO_2$. For example, under comparable CVD conditions, use of a $Si_3N_4$ surface layer may yield fewer and shorter nanotubes in comparison to a $SiO_2$ surface.

Surface layer 206 may be configured to promote desired nanotube growth. In particular, $SiO_2$ may be readily formed as a layer having a smooth surface texture at nanometer scales, so as to provide a suitable surface for the growth of a nanotube network. For example, a layer 206 of $SiO_2$ may be vapor deposited so as to present a nano-scale smooth surface morphology. A strong positive correlation of nanotube growth success with surface smoothness is believed to exist for a range of substrate surface textures and materials, including thermally grown $SiO_2$, CVD-formed $SiO_2$, $Si_3N_4$, and amorphous $SiO_2$. That is, the smoother the surface used for CVD nanotube growth, the longer the resulting nanotube. This correlation may be directly observed by atomic force microscopy (AFM) or other methods. It is believed that nanotube growth under CVD conditions as known in the art includes the tubes being "spun" out from metal particles supersaturated with carbon. Surface roughness tends to inhibit nanotube growth, as the higher incidence of surface defects and features tends to interact with growing nanotubes so as to stop the nanotube growth process. In an embodiment of the invention, a surface layer favoring nanotube growth comprises a layer of $SiO_2$ from about 50 to about 2000 nm thick, and more preferably from about 50 to about 1000 nm thick, optionally over a diffusion-blocking layer as described above. A suitable $SiO_2$ layer may be formed by methods such as CVD, EPCVD or other suitable method, as known in the art.

In some embodiments, a diffusion barrier 222 and a surface layer 206 may be combined into an integrated layer. A suitable integrated surface layer may comprise a material which has a high dielectric properties, high metal diffusion resistance and a very smooth surface texture. For example, a film having a selected dielectric constant and high metal diffusion resistance, such as a $Si_3N_4$ as described above, may be formed upon a bulk semiconductor substrate. The deposited film may then be modified to a desired level of smoothness using CMP, thermal annealing, or any other suitable method. In the alternative, the barrier film may be deposited by a method producing a smooth surface as deposited, such as by using a high density plasma deposition system where sputtering and deposition occur simultaneously.

Optimum dimensions and properties of a suitable diffusion barrier layer 222 and a surface layer 206 favoring nanostructure fabrication may be specific to particular devices, applications, architectures and operating conditions. For example, for a nanosensor embodying a nanotube field effect transistor, gate voltage, gate leakage current, on-off current ratio, or other operational characteristics of the completed nanosensor may be influenced by the properties of the diffusion barrier layer 222 and surface layer 206. One of ordinary skill in the art may appropriately adjust the thickness, composition and other properties of either or both of the diffusion barrier layer 222 and a surface layer 206 to maintain the properties of such a nanosensor device within selected limits, based on the disclosure herein.

6. Pre-Patterned Fabrication Substrates

A wafer embodiment having aspects of the invention may comprise a pre-patterned semiconductor substrate wafer (e.g., silicon), preferably of generally conventional semiconductor wafer size, shape, thickness and other characteristics, so as to be suitable for processing, treating, cleaning, masking, testing and handling by conventional semiconductor-fabrication equipment. The wafer may comprise at least one contaminant-protective layer or diffusion barrier such as described herein covering the bulk substrate on at least an upper side of the wafer. The wafer may further comprise a nanostructure growth-favoring layer such as also described herein overlaying the contaminant-protective layer. The wafer embodiment should be suitable as an intermediate product for the making of nanosensors or other nanoelectronic devices.

Optionally, the wafer may include a pre-deposited dispersal of a nanostructure growth-favoring composition such as described herein disposed upon the substrate. In certain embodiments, the growth promoter may be arranged at selected sites or patterned in areas where nanostructure growth is desired. Likewise, the growth promoter may be excluded from areas in which nanostructure growth is not desired.

Also optionally, the wafer may comprise a pre-deposited pattern of conductors, electrodes, or other electronic devices or elements upon or adjacent to at least an upper wafer surface. A suitable electrode pattern may include electrodes for a plurality of nanosensors, for example disposed in an array or for fabricating multiple nanosensor devices on a single wafer. Wafer-level fabrication may be advantageous for manufacturing both single sensors and integrated arrays of sensors.

According to the foregoing a method embodiment may comprise, in any operative order, the steps of:
a) providing a pre-fabricated semiconductor wafer (e.g., silicon);
b) forming at least one contaminant-protective layer upon the bulk substrate on at least an upper side of the wafer;
c) forming a conditioned surface layer disposed on at least an upper side of the wafer;
d) optionally forming a pattern or dispersal of a nanostructure growth promoter composition disposed upon or adjacent at least an upper side of the wafer; and
e) optionally forming a pattern of conductors, electrodes, or other device elements disposed upon or adjacent at least an upper side of the wafer.

7. Encapsulated Nanosensor

Figure 4:
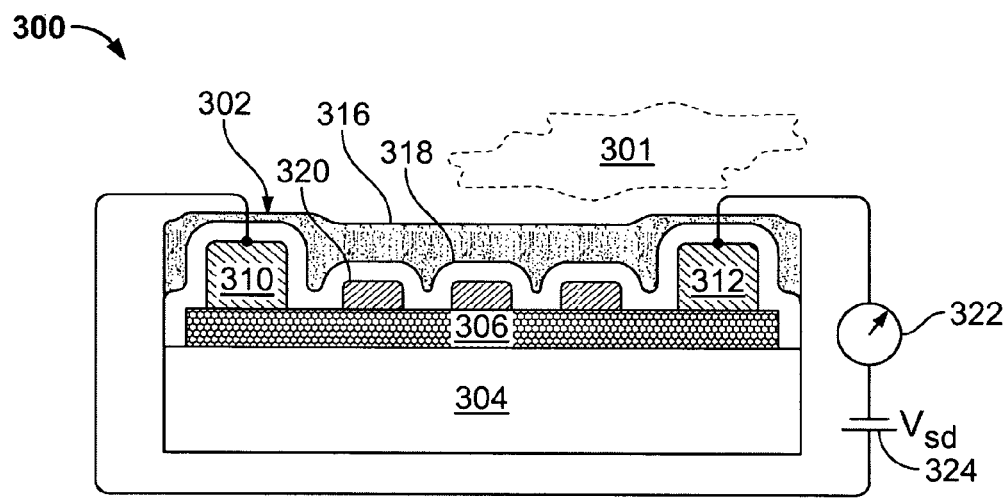
FIG. 4 is a schematic side view showing an encapsulated nanosensor and associated circuit elements.

FIG. 4 shows an exemplary sensing device 300 and nanosensor 302, wherein the nanosensor is encapsulated. Sensing device 300 comprises a nanostructure sensor 302 comprising an insulating substrate 304. Insulating substrate 304 may comprise a dielectric material, such as fused quartz or other suitable material. Dielectric substrate 304 provides electrical isolation of the channel 306 and source and drain contacts 310, 312. Optionally, a separate dielectric layer or other electrical isolation element may be included (not shown). Channel 306 may comprise a carbon nanotube network grown by CVD directly upon the substrate 304 by the methods described above. Optionally, a conditioned surface layer can be included to favor nanotube growth.

Nanosensor 302 may further comprise an optional passivation layer 318 comprising $SiO_2$ or other suitable material. The passivation layer 318 (if present), electrodes 310, 312 and nanotube channel 306 may be covered by an encapsulation material 316, such as a polymer coating. The composition or configuration of the passivation layer 318 or encapsulation layer 316 may be controlled to achieve a desired degree of interaction of a target analyte 301, for example gaseous hydrogen in air, with functionalization material 320 adjacent nanostructure channel 306. Thus, the sensitivity of the nanosensor 302 to the analyte may be controlled by controlling the diffusion rate of the target analyte through layers 316 and 318. In addition, these layers may be configured to exclude or reduce diffusion of non-target species. For example, suitable passivation and encapsulation layers may be useful in reducing cross-sensitivity or humidity sensitivity.

The sensor device 300 may comprise suitable circuitry and instrumentation to perform measurements of the electrical response of nanostructure sensor 302 to analyte 301. Such circuit elements are represented schematically as a voltage source 324 ($V_{sd}$), and measurement instrumentation 322. Although no gate electrode is shown in FIG. 4, a gate electrode and associated elements as described herein may optionally be included.

Encapsulation. As shown in FIG. 4, encapsulation layer 316 may cover all or a portion of nanosensor device 302. Encapsulation layer 316 may comprise an electrical insulating material such as $SiO_2$, SiO, $Si_3N_4$, $Al_2O_3$, or an organic layer such as parylene, organic polymer, hydrophobic polymers such as fluoropolymers, or a combination of such materials. The encapsulation layer 316 may be selected so as to reduce cross sensitivity or to act as a water barrier in order to reduce water-induced response variations. A further function of layer 316 may be to protect the device 302 from mechanical damage. Encapsulation layer 316 may comprise a multilayer or composite structure. A multilayer composite of differing materials, such as an $Al_2O_3$/polymer composite, may reduce the diffusion of water by multiple orders of magnitude. Such an encapsulation structure may be more effective than a thicker layer of one material alone, because it reduces the possible number of pathways, such as pinholes or cracks, for non-target analytes or solvents.

In nanosensor embodiments for $H_2$ sensing, an encapsulation layer as described herein may be necessary to prevent the response of the device from being dependant on the relative humidity of the sample medium, e.g. ambient air. That is, encapsulation layer 316 may prevent or reduce variation in sensor response induced by the relative humidity, for hydrogen and other analytes.

In addition, an encapsulation layer 316 may increase the specificity of the sensor to hydrogen or other penetrating analytes in contrast to other, less penetrating analytes. Since hydrogen is highly diffusive, $H_2$ may pass easily through an encapsulation layer which is generally impermeable to other (typically larger) molecules that may be present in the sample medium. For example, it may be found that without a suitable encapsulation layer, a large variation of the conductance of the sensor may occur in response to gases such as $NH_3$ or $NO_2$. Since molecules of such gases are much larger than hydrogen molecules, an encapsulation layer may be readily configured to eliminate or substantially reduce such cross-sensitivity.

In an embodiment of the invention, an encapsulation layer 316 may comprise about 1 to about 3 μm of AFP4 over a passivation layer 318 of about 5 nm thickness of $SiO_2$. An alternative encapsulation structure may comprise about 1 to 3 μm of AFP4 over about 5 to about 15 nm of $Al_2O_3$. The addition of such an encapsulation layers should not greatly reduce the sensor sensitivity or response time to hydrogen. Such encapsulation layers may also increase the useful lifetime of the sensor. Passivation layer 318 may be configured as described above in connection with FIGS. 1 and 3B.

As candidate encapsulation materials, polymers have the additional advantage of being readily processable using procedures such as spin coating, dip coating, drop casting, and microspotting. Microspotting, in particular, may be useful for fabrication of multiple sensor in a sensor array that is configured to respond to a variety of different analytes. Yet another advantage is that polymer coatings often modify the characteristics of NTFET devices, which can be monitored during processing for control of coating processes.

EXAMPLE A

Figure 5:
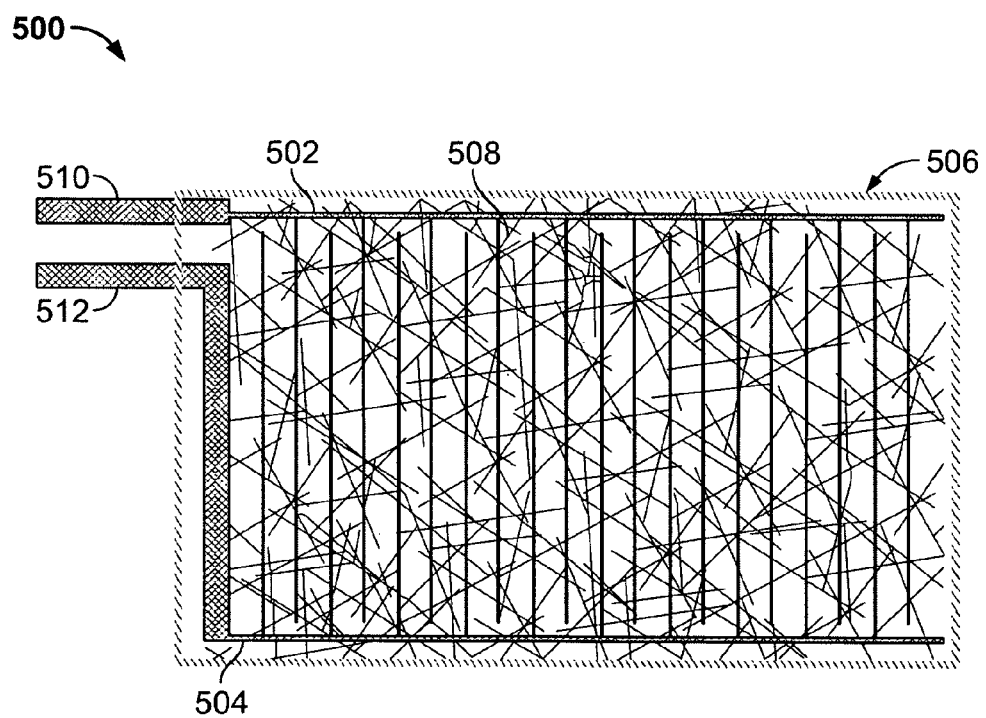
FIG. 5 is a schematic diagram showing an exemplary design for a nanostructure sensor using a random network of nanotubes.

Nanotube Network $CO_2$ Sensor with remote measurement circuitry. An exemplary NTFET $CO_2$ sensor with remote measurement circuitry was prepared as follows. A degenerately doped silicon wafer with a silicon oxide film was coated with carbon nanotubes in a random network, as described in the above-incorporated application Ser. No. 10/177,929. A plurality of nanosensor devices 500 were thus formed, one of which is shown schematically in FIG. 5. Titanium contacts 35 nm thick covered with gold contacts 100 nm thick were deposited and patterned by photolithography and lift-off to form opposing contacts 502, 504. Contacts 502, 504 each comprised a plurality of interdigitated portions disposed over a generally rectangular region 506. A network of randomly oriented nanotubes 508 was disposed over the silicon substrate in electrical contact with interdigitated portions of contacts 502, 504.

After the deposition of the contacts 502, 504 and network 508, nanotubes outside of the generally rectangular area 506 were removed by oxygen plasma etching, isolating nanotube network 508 from similar networks of adjacent nanosensor devices on the wafer. The use of interdigitated sets of metal electrodes 502, 504 with nanotube network 508 interposed generally between the interdigitated contacts resulted in many nanotubes connected in parallel across the electrodes. Conductance between the electrodes 502, 504 was measured as a function of gate voltages between ±10 V. The maximum conductance was approximately 10 kΩ, and the on-off ratio was approximately 10.

To facilitate mass production, the above described process may be carried out on a plurality of sensors in parallel fashion, such that multiple copies of the sensor geometry are arranged over the wafer, each copy being made as an individual sensor die that can be separated from the wafer or diced for further packaging into a completed measurement apparatus. Each die may be mounted in a standard chip package, such as a standard 16-pin chip carrier, for subsequent incorporation into measurement circuitry. In the alternative, a die may be mounted directly onto a circuit board. For example, a sensor die may be mounted directly on a printed circuit board, with wires connecting the interdigitated wires on the chip to contacts on the printed circuit board.

A die was separated from the wafer and mounted in a standard 16-pin chip carrier, with wires connecting the interdigitated electrodes of the nanosensor device to the contacts on the chip carrier. Polyethylene imine was deposited by drop-casting, as described in the above-referenced application Ser. No. 10/940,324, to make the nanostructure electronic device into a nanostructure sensor for carbon dioxide. Several calibration values were measured, at which the electrical resistance of the sensor was recorded in the presence of a known concentration of carbon dioxide.

Figure 6:
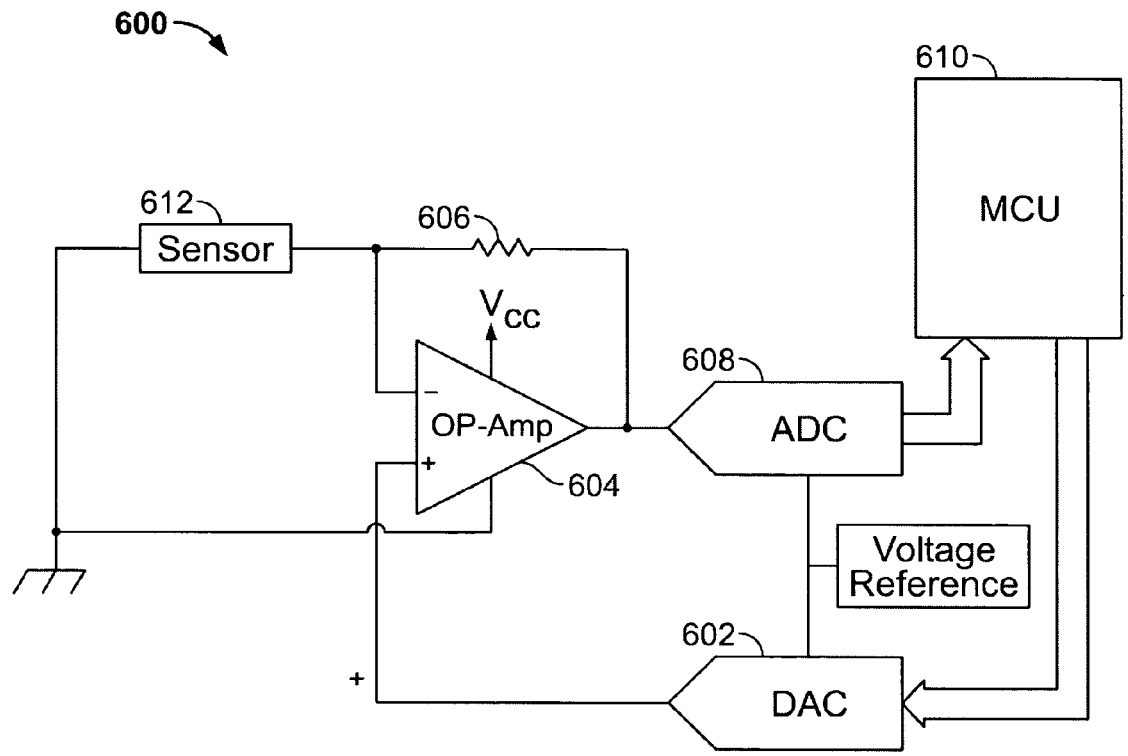
FIG. 6 is a schematic circuit diagram showing an exemplary electronic circuit for a remote sensing device according to an embodiment of the invention.

An electronic circuit 600 was built as shown in FIG. 6. A 10-bit digital-to-analog ("DAC") converter 602 (e.g., Maxim part 5841MEUB) supplied a voltage of 100 mV as a bias voltage across the two interdigitated electrodes 502, 504 of device 500. An inexpensive op-amp 604 served as a buffer of this bias voltage. Precision resistor 606 converted the current through the nanostructure sensor into a voltage, which was measured by a 12-bit analog-to-digital converter 608 (e.g., Maxim part 1237). The digital output of the converter was recorded by a microprocessor 610 (e.g., Texas Instruments part MSP430F149). The microprocessor had previously been loaded with the measured calibration values of the sensor. Using these values, it converted the digital output of the converter into a measured concentration of carbon dioxide.

The microprocessor communicated data to a radio communications control chip (e.g., Chipcon part CC2420, not shown). The radio communications control chip transmitted the carbon dioxide concentration at a radio frequency of 2.4 GHz, using the 802.15.4 standard for radio communication. A base station (e.g., Chipcon part CC2420 integrated with a computer) received the data communicating the carbon dioxide concentration. A battery supplied power to the remotely communicating device.

This example is relevant to the application of capnography, which is the measurement of carbon dioxide in human breath during the giving of medical care. The invention enables capnometry to be performed without connecting wires from a patient's carbon dioxide sensor to a recording instrument. Thus, the patient can move and be moved freely while the capnometry proceeds.

EXAMPLE B

Nanotube Network $H_2$ Sensor with remote measurement circuitry. The process as described above in Example A, except for deposition of polyethylene imine, was carried out construct a bare (non-functionalized) nanosensor device. Over a range of gate voltages between +10 V and −10 V, the maximum conductance of the bare device was approximately 10 k$\Omega$, and the on-off ratio was approximately 10. Many such devices were constructed on individual dies of a wafer. To functionalize for hydrogen, palladium metal was deposited on the substrate and patterned using photolithography and lift-off, as described above.

A selected die was separated from the wafer and mounted in a standard 16-pin chip carrier. Wires were used to connect leads 510, 512 to the contacts on the chip carrier, which connected to measurement circuitry on a prototype circuit board. The measurement circuit 600 was constructed as diagrammed in FIG. 7, using integrated circuit chips mounted on the same circuit board as the sensor die. A microprocessor 702 was selected (e.g., Texas Instruments part No. MSP430F1232), which includes an integrated 10-bit analog-to-digital converter 704 and a voltage source 706. The voltage source 706 applied a bias voltage across the nanostructure sensor 708 in series with a resistor 710. The analog-to-digital converter measured the voltage across the resistor 710 and converted this voltage into a digital signal.

Note that in alternative embodiments, voltage source 706 may be omitted, and a voltage source of the analog-to-digital converter 704 may be used alone. Ratiometric measurement may be employed wherein the sensor voltage change is measured as a fraction of the total voltage change of nanostructure sensor 708 in series with a resistor 710.

The microprocessor recorded the digital signal. Given the known value of the resistor and the digital signal recording the voltage across the resistor, the microprocessor calculated the current through the resistor. Given the known reference voltage from source 706 and the digital signal recording the voltage across the resistor, the microprocessor calculated the voltage across the nanostructure sensor 708. Based on the voltage across the nanostructure sensor and the current through the resistor, the microprocessor calculated the resistance of the nanostructure sensor.

The microprocessor had previously been loaded with the measured calibration value of the nanostructure sensor. In this example, several calibration values were measured, at which the electrical resistance of the sensor was recorded in the presence of a known concentration of hydrogen in air. The microprocessor used these values to convert the measured resistance of the sensor into a concentration of hydrogen.

The microprocessor communicated data to a radio communications control chip (e.g., Chipcon part CC2420, not shown). The radio communications control chip transmitted the hydrogen concentration at a radio frequency of 2.4 GHz, using the 802.15.4 standard for radio communication. A base station (e.g., Chipcon part CC2420 integrated with a computer) received the data communicating the hydrogen concentration. A battery supplied power to the remotely communicating device.

Figure 7:
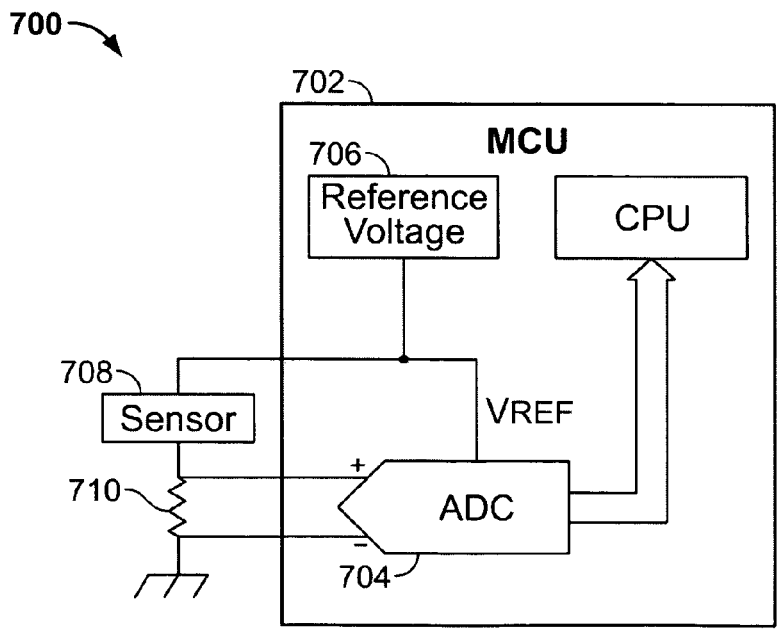
FIG. 7 is a schematic circuit diagram showing an exemplary electronic circuit for a remote sensing device according to an alternative embodiment of the invention.

Note that in the example of FIG. 7, there may be no amplification or other processing of the signal form sensor 708 prior to communication to analog-to-digital converter 704. The capability of nanosensors having aspects of the invention to provide a useful signal directly for a simple, low cost assembly (in addition to conserving power) makes the sensor particularly suitable for use with commercially available integrated remote/distributed communication chips. IC chips are available which include an integral analog-to-digital converter, microprocessor and radio transceiver. The nanosensor may be directly connected to the ADC contacts of the IC.

Figure 8:
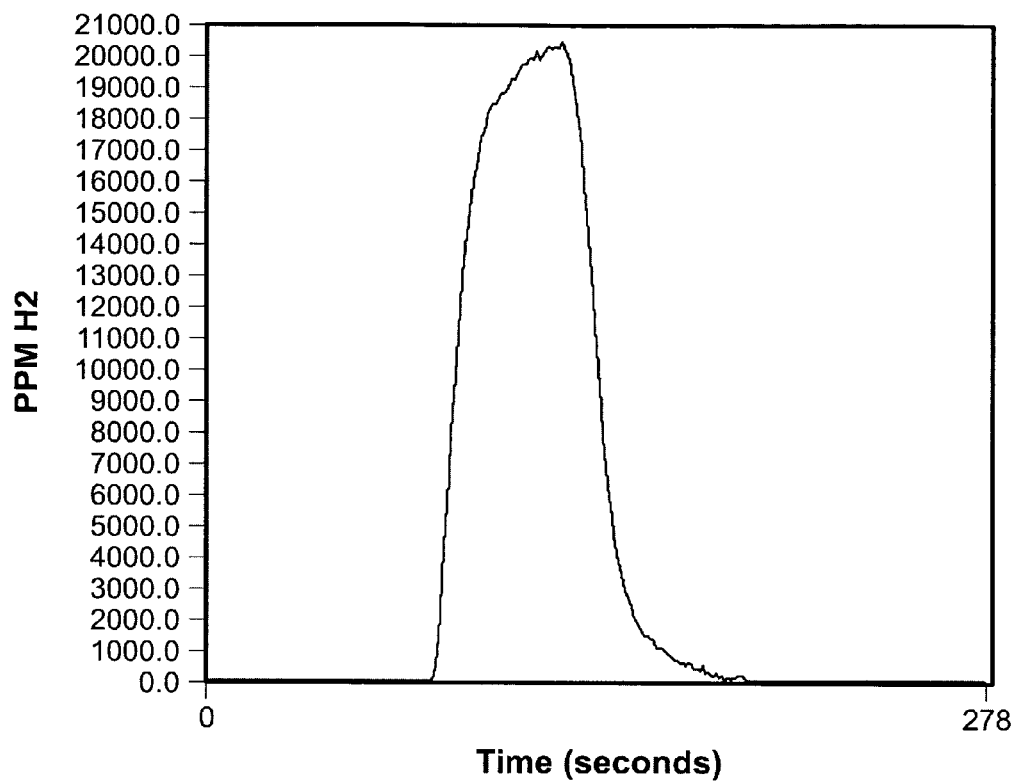
FIG. 8 is a chart showing an exemplary signal from an exemplary battery-powered hydrogen sensor, transmitted by a radio antenna and received by a base station.

FIG. 8 is a plot showing a measurement by an exemplary sensor system embodiment constructed generally as described in this example. The plot shows calibrated values of $H_2$ as parts-per-million (ppm) in air versus time. It can be seen that upon exposure the $H_2$ (in this case at a concentration of about 20,000 ppm or about 2%), the sensor rapidly responds to an asymptotic output value. As hydrogen exposure is removed, the sensor rapidly recovers to its pre-exposure reading.

Figure 9:
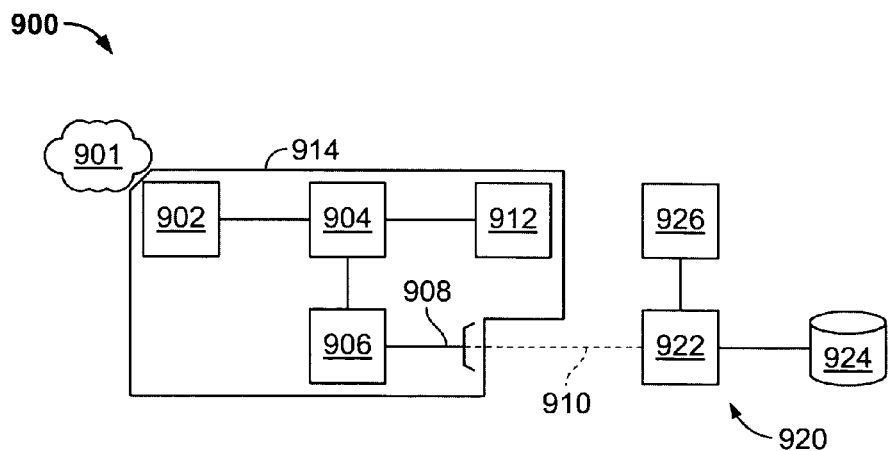
FIG. 9 is a block diagram showing an exemplary arrangement of elements for a remote sensing system according to the invention.

In summary of the foregoing, a remotely-operating, battery powered nanostructure sensor device 900 may comprise a nanosensor 902 for sensing an analyte 901, as shown in FIG. 9. Nanosensor 902 may comprise any suitable sensor incorporating a nanostructure material as an electronic sensing element for an analyte, including but not limited to the $H_2$ and $CO_2$ sensor embodiments described herein. Sensor device 900 may further comprise a measurement circuit or processor 904 configured for receiving a signal from the nanosensor 902. Processor 904 may be adapted for operating the sensor and for analyzing the sensor signals to derive useful information regarding the presence or absence of a targeted analyte in the remote environment. In the alternative, the processor or circuit 904 may merely handle signal data without analyzing it. Processor 904 may be operatively associated with a memory as known in the art. The memory may hold software or firmware used for programming the operation of the processor and measurement circuit.

Processor 904 may be connected to any suitable transmitter 906 for transmitting a wireless signal 910 via any suitable emitter 908. Suitable wireless signals may include, for example, radio frequency signals, infrared signals, optical signals, or and other suitable wireless signal as known in the art. The wireless signal should be selected to meet the needs of the application. For example, for short-range wireless transmission, a low-power RF signal may be appropriate. For transmission over long distances, more sophisticated transmission schemes may be used.

The use of a wireless data signal 910 and transmitter 906 advantageously permits device 900 to be a mobile unit. To this end, device 900 may be powered by a battery 912 as known in the art. In the alternative, or in addition, a portable power source such as a solar electric cell or a fuel cell may be used.

The nanosensor 902, circuit 904, transmitter 906, and portable power source 912 may be assembled together in a portable unit 914. For example, these components may be placed on one or more circuit boards, which may be assembled into a suitable housing. In the alternative, all of the components of a sensor 900 may be provided in a single semiconductor device of a very small size, such as less than a few millimeters on a side. Power may be supplied via a small battery, or may be beamed wirelessly to devices within range of a base station. It should be appreciated that the invention disclosed herein should permit the development of very small portable sensors. One of ordinary skill may develop various suitable ways for packaging a nanostructure sensor device 900 for portable wireless operation.

The wireless signal 910 may be received by a base station 920. The base station may comprise a receiver/processor 922 for receiving the signal 910 and processing the signal according to system software or firmware. In addition, base station 920 may comprise a memory or data storage unit 924, which may be used to maintain a record of past sensor data. Base station 920 may also comprise a user interface 926, which may comprise an input device such as a keyboard and an output device such as a display screen or the like. Various suitable user interface systems are known in the computing arts. The base station 920 may be used to service the ultimate end-user of the sensor data, such as a medical station or environmental control station. In the alternative, or in addition, the base station may be used to relay data from one or more portable sensor devices 900 to a more remote location, via any suitable wired or wireless connection. A single base station may be used to receive data from one or more sensor devices 900. A base station may also include a transmitter, and be used to transmit data, commands, or other information to one or more sensor devices 900 equipped with a corresponding receiver.

Having thus described a preferred embodiment of the remotely communicating, battery-powered nanostructure sensor device, it should be apparent to those skilled in the art that certain advantages of the within system have been achieved. It should also be appreciated that various modifications, adaptations, and alternative embodiments thereof may be made within the scope and spirit of the present invention. The invention is defined by the following claims.

What is claimed is:

1. A remote sensor device, comprising:
   a nanostructure sensor comprising a nanostructure conducting channel between a source electrode and a drain electrode, wherein the nanostructure sensor is configured to respond to an analyte;
   a measurement circuit operatively connected to the nanostructure sensor, the measurement circuit configured to provide a signal indicating a response of the nanostructure sensor to the analyte; and
   a transmitter operatively connected to the measurement circuit, the transmitter configured to wirelessly transmit the signal,
   wherein the nanostructure sensor, the measurement circuit, and the transmitter are assembled together in a portable unit.

2. The remote sensor device of claim 1, further comprising a portable power source connected to provide power to the measurement circuit.

3. The remote sensor device of claim 2, wherein the portable power source is selected from the group consisting of a battery, a solar cell, and a fuel cell.

4. The remote sensor device of claim 1, wherein the measurement circuit further comprises a processor configured to determine an amount of the analyte based on the signal from the nanostructure sensor.

5. The remote sensor device of claim 1, wherein the nanostructure conducting channel comprises a nanotube.

6. The remote sensor device of claim 1, wherein the nanostructure conducting channel comprises a network of randomly-oriented nanotubes.

7. The remote sensor device of claim 6, wherein the source electrode comprises a plurality of fingers interdigitated with fingers of the drain electrode.

8. The remote sensor device of claim 1, further comprising a functionalization material disposed adjacent to the nanostructure conducting channel.

9. The remote sensor device of claim 8, wherein the functionalization material comprises a material selected from palladium and polyethylene imine.

10. The remote sensor device of claim 1, further comprising an encapsulation material covering the nanostructure conducting channel, the source electrode, and the drain electrode, wherein the encapsulation material is configured to control a diffusion rate of the analyte through the encapsulating material.

11. The remote sensor device of claim 1, further comprising a base under the nanostructure conducting channel, the source electrode, and the drain electrode, wherein the base is selected from a semiconducting material and an insulating material.

12. The remote sensor device of claim 11, further comprising a passivation layer interposed between the nanostructure conducting channel and the base.

13. The remote sensor device of claim 11, further comprising a diffusion blocking layer interposed between the base and at least one of the source and drain electrodes.

14. The remote sensor device of claim 13, wherein the diffusion blocking layer comprises a $Si_3N_4$ layer.

15. The remote sensor device of claim 13, further comprising a conditioned surface layer overlying the diffusion blocking layer.

16. The remote sensor device of claim 13, wherein the conditioned surface layer comprises an $SiO2$ layer.

17. The remote sensor device of claim 1, wherein the nanostructure sensor comprises a plurality of electrically isolated sensors configured to respond to the analyte.

18. The remote sensor device of claim 1, wherein the nanostructure sensor comprises a plurality of electrically isolated sensors configured to respond to different analytes.

19. The remote sensor device of claim 1, wherein the nanostructure sensor comprises at least a first nanostructure capacitor element disposed spaced-apart from at least a corresponding second capacitor element.

20. The remote sensor device of claim 1, wherein one or more of the nanostructure sensor, at least a portion of the measurement circuit and at least a portion of the transmitter is included in an integrated circuit chip.

21. The remote sensor device of claim 1, wherein the measurement circuit includes an analog-to-digital converter, and wherein the nano structure sensor communicates directly to the analog-to-digital converter without intermediate signal amplification.

22. The remote sensor device of claim 8, wherein the functionalization material is patterned to cover a portion of the nanostructure conducting channel and to leave a remaining part of the nanostructure conducting channel exposed to the analyte.

23. The remote sensor device of claim 11, wherein the base comprises a porous material, wherein the porous material comprises a plurality of channels configured to permit suction to be applied across the base.

24. A system for collecting information regarding a remote analyte, the system comprising:
   a sensor device, comprising
      a nanostructure sensor comprising a nanostructure conducting channel between a source electrode and a drain electrode,
      a measurement circuit operatively connected to the nanostructure sensor configured to provide a signal indicating a response of the nanostructure sensor to an analyte,
      a wireless transmitter operatively connected to the measurement circuit; and a base station comprising a wireless receiver located remotely from the sensor device and configured to wirelessly receive the signal from the sensor device.

25. The system of claim 24, further comprising a portable power source for the sensor device.

26. The system of claim 24, further comprising a plurality of sensor devices each comprising a nanostructure sensor, wherein the base station is configured to wirelessly receive signals from the plurality of sensor devices indicating a response of each sensor to analytes.

27. The system of claim 24, wherein the base station further comprises a transmitter adapted for wirelessly relaying the signal to a second remote station.

28. The system of claim 24, wherein the base station further comprises an output device adapted for providing a user with information concerning an amount of analyte measured by the sensor device.

* * * * *